United States Patent
Scheider et al.

[19]

[11] Patent Number: 6,112,581
[45] Date of Patent: Sep. 5, 2000

[54] VIBRATORY VISCOMETER

[75] Inventors: Gerard Scheider, Parlin; John L. Batton, Metuchen; John S. Vilichka, Portreading, all of N.J.

[73] Assignee: National Metal Refining Company, Metuchen, N.J.

[21] Appl. No.: 08/926,849

[22] Filed: Sep. 10, 1997

[51] Int. Cl.[7] .......................... G01N 11/16; G01N 11/00; B22D 11/06
[52] U.S. Cl. .......................... 73/54.24; 73/54.28; 73/592
[58] Field of Search ................... 73/54.24, 54.28, 73/54.25, 592

[56] References Cited

U.S. PATENT DOCUMENTS

| | | | |
|---|---|---|---|
| 2,518,348 | 8/1950 | Mason | 73/54 |
| 2,701,469 | 2/1955 | Burns, Jr. | 73/59 |
| 3,062,040 | 11/1962 | McKennell et al. | 73/59 |
| 3,131,515 | 5/1964 | Mason | 581/58 |
| 3,382,706 | 5/1968 | Fitzgerlad et al. | 73/59 |
| 3,393,553 | 7/1968 | Kleinschmidt | 73/54 |
| 3,710,614 | 1/1973 | Opplinger | 73/59 |
| 3,712,117 | 1/1973 | Fitzgerald et al. | 73/59 |
| 3,734,119 | 5/1973 | Nudds | 137/92 |
| 3,762,429 | 10/1973 | Fitzgerald et al. | 137/92 |
| 3,875,791 | 4/1975 | Fitzgerald et al. | 73/59 |
| 4,299,119 | 11/1981 | Fitzgerald et al. | 73/59 |
| 4,488,427 | 12/1984 | Matsuik et al. | 73/59 |
| 4,524,610 | 6/1985 | Fitzgerald et al. | 73/54 |
| 4,566,181 | 1/1986 | Matsuik et al. | 29/602 R |
| 4,703,174 | 10/1987 | Anderson et al. | 250/227 |
| 4,754,640 | 7/1988 | Fitzgerald et al. | 73/54 |
| 4,763,512 | 8/1988 | Taylor | 73/54 |
| 4,905,499 | 3/1990 | Miura et al. | 73/32 A |
| 5,036,901 | 8/1991 | Williams et al. | 164/452 |
| 5,054,313 | 10/1991 | Fitzgerald et al. | 73/59 |
| 5,337,234 | 8/1994 | Anderson et al. | 364/422 |
| 5,445,035 | 8/1995 | Delajoud | 73/861.52 |
| 5,670,709 | 9/1997 | Gallagher | 73/54.24 |
| 5,710,374 | 1/1998 | Ross et al. | 73/54.24 |

*Primary Examiner*—Hezron Williams
*Assistant Examiner*—J. David Wiggins
*Attorney, Agent, or Firm*—Fish & Richardson P.C.

[57] ABSTRACT

A transducer for a vibratory viscometer includes a hollow cylindrical sheath and a hollow cylindrical shaft disposed within the cylindrical sheath. The shaft has a first end portion and a second end portion connected to a distal end portion of the sheath. The viscometer includes a sensor tip connected to the distal end portion of the sheath. The sensor tip has an inner surface defining a hollow region and a support tube disposed within the hollow region configured to hold a temperature sensor. The viscometer further includes a crossbar coupled to the first end portion of the shaft.

28 Claims, 8 Drawing Sheets

VIBRATORY VISCOMETER

FIELD OF THE INVENTION

This invention relates to a vibratory viscometer for measuring the viscosity of a fluid.

BACKGROUND OF THE INVENTION

In many commercial processes, in-line viscometers monitor and measure the viscosities of the fluids involved in the processes on a continuous or on an operator demand basis. To this end, rotational vibratory viscometers have enabled the measurement of liquid viscosities over a wide range with significant accuracy and precision.

SUMMARY OF THE INVENTION

In accordance with the invention, a transducer for a vibratory viscometer includes a sensor tip that includes a cylindrical member having an inner surface defining a hollow region and an opening to the hollow region. A support tube is disposed within the sensor tip and configured to hold a temperature sensor.

In another aspect of the invention, a sensor tip for a viscometer includes a spherical member having an inner surface defining a hollow region. The sensor tip has a hollow bore configured to hold a temperature sensor. The spherical member is sealed so that both hollow regions are isolated from a fluid into which the member is immersed.

In another aspect of the invention, a transducer for a vibratory viscometer includes a hollow cylindrical sheath and a hollow cylindrical shaft disposed within the cylindrical sheath. The shaft has a first end portion and a second end portion connected to a distal end portion of the sheath. The viscometer includes a sensor tip connected to the distal end portion of the sheath. The sensor tip has an inner surface defining a hollow region and a support tube disposed within the hollow region configured to hold a temperature sensor. The viscometer further includes a crossbar coupled to the first end portion of the shaft.

In yet another aspect of the invention, a method of measuring viscosity of a fluid includes providing a transducer with a hollow sensor tip having a support tube and a temperature sensor disposed within the support tube, and with the support tube disposed within the sensor tip. The sensor tip is immersed into the fluid, and electrical power drives the transducer causing the sensor tip to oscillate about its axis. The oscillation of the sensor tip is maintained at a predetermined amplitude by varying the electrical power. Finally, the electrical power applied to the transducer is correlated to the viscosity of the fluid.

Implementations of the invention may provide one or more advantages. For example, the hollow sensor tip provides the ability to measure fluid viscosities with greater sensitivity because less mass is being driven as compared to a solid tip sensor of the same size. Also, there is less thermal mass associated with a hollow sensor tip such that with a temperature sensor disposed within the tip sensor, the response time to measure the temperature (or temperature fluctuations) is reduced.

BRIEF DESCRIPTION OF THE DRAWINGS

The foregoing features and other aspects of the invention will be described further in detail by reference to the accompanying drawings, in which.

DESCRIPTION OF THE PREFERRED EMBODIMENTS

Figure 1:
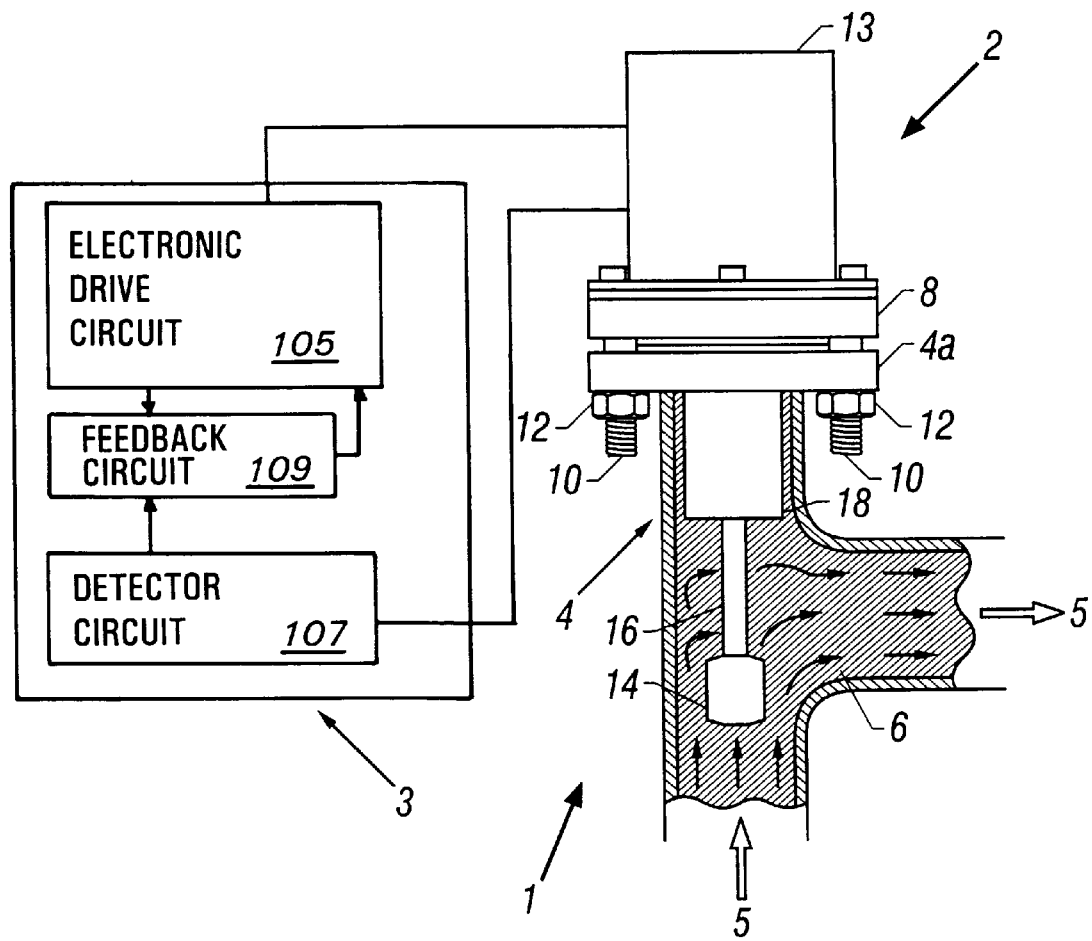
FIG. 1 is a schematic view of a viscosity measuring system.
Figure 2A:
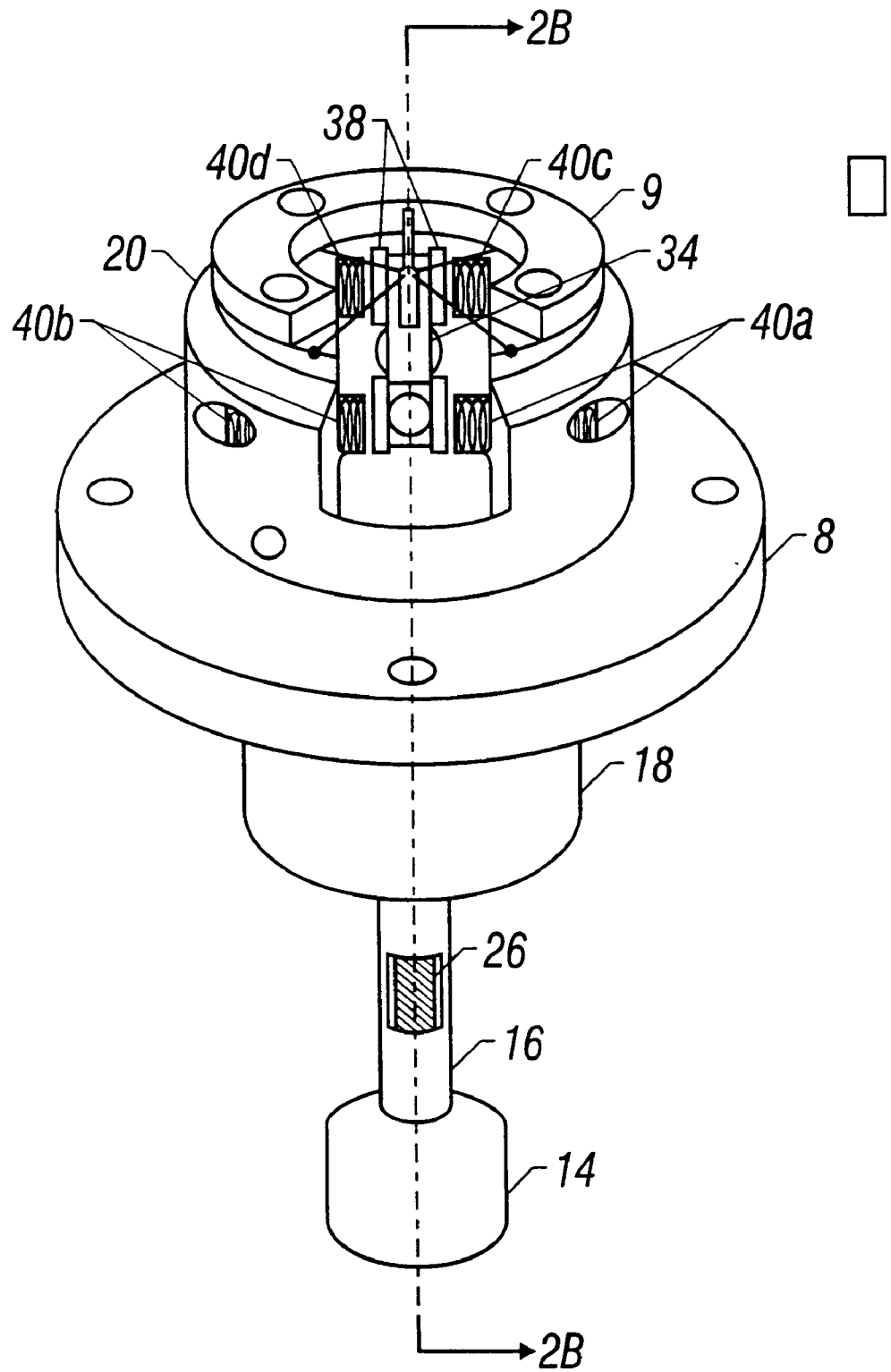
FIG. 2A is a partially cross-sectional perspective view of a viscometer transducer.
Figure 2B:
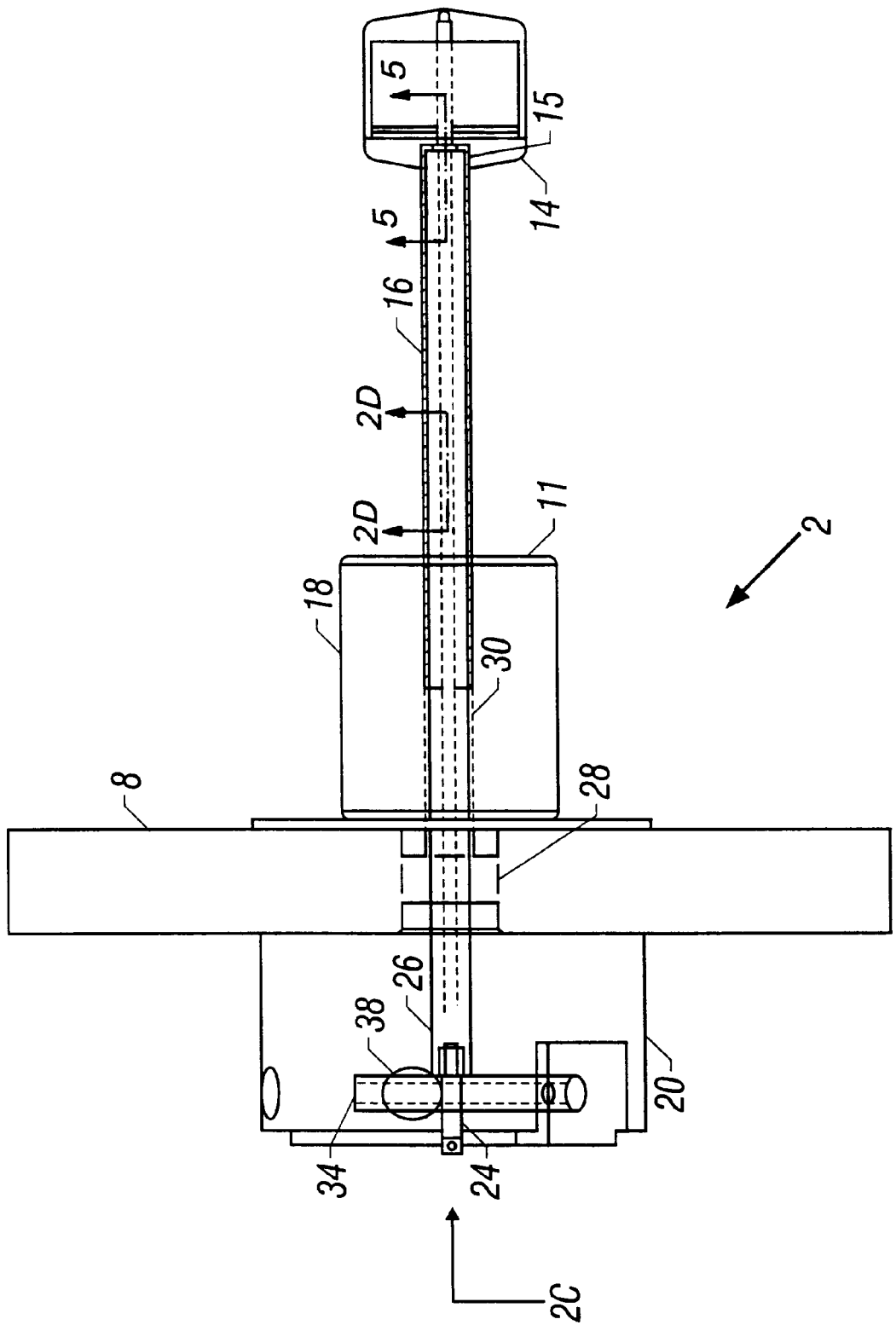
FIG. 2B is a side cross-sectional view of the viscometer taken along line 2B—2B of FIG. 2A.
Figure 2C:
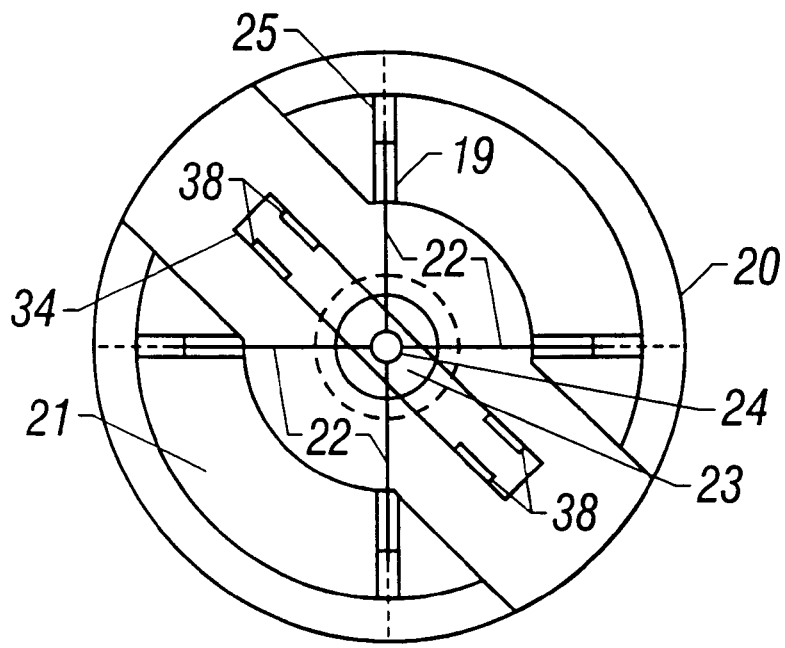
FIG. 2C is a top view of the viscometer taken along line 2C of FIG. 2B.
Figure 2D:
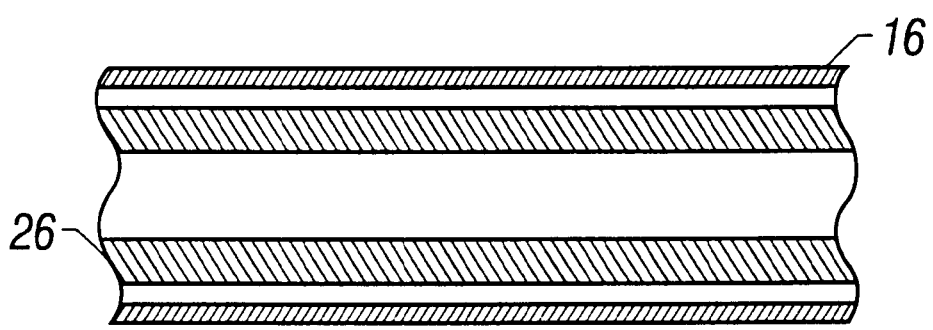
FIG. 2D is an enlarged view along line 2D—2D of FIG. 2B.

Referring to FIG. 1, a viscometer 1 includes a transducer 2 positioned on a flow pipe 4 to measure the viscosity of a fluid 6 flowing through pipe 4 in the general direction of arrows 5. Transducer 2 includes a flange 8 in secured engagement with a flange portion 4a of pipe 4. Flange 8 is fastened to flange portion 4a by bolts 10 in threaded engagement with nuts 12. Alternatively, flange 8 may include threaded mounting studs (not shown) extending from the lower surface of flange 8. The threaded mounting studs would be used in place of bolts 10. Transducer 2 also includes a dome cover 13 attached to flange 8 that covers and protects the inner components of the transducer. Dome cover 13 includes a lid (not shown) to provide accessibility to the inside of the transducer. Dome cover 13 may include cooling ports to prevent the inner components from over heating.

Transducer 2 is connected to a controller 3 which controls and also monitors the signal output from transducer 2. A suitable controller is described in U.S. Pat. No. 5,054,313, which is hereby incorporated by reference as if it was fully set forth. The controller includes a drive circuit 105 and a detector circuit 107. Drive circuit 105 supplies electrical power to transducer 2 causing a sensor tip 14 of transducer 2 to oscillate about the axis of sensor tip 14, while detector circuit 107 detects the amplitude of the oscillations. Signals from both drive circuit 105 and detector circuit 107 are fed into a feedback circuit 109 to provide correction signals to drive circuit 105 so that the oscillation amplitude of the sensor tip is maintained at a specified value. The electrical power supplied to transducer 2 by drive circuit 105 is correlated to the viscosity of the fluid by comparing the power required to drive the system at a predetermined amplitude to that which is required to drive the system at the same amplitude in a series of NIST (National Institute of Standards and Technology) traceable viscosity standards.

The operation and performance of the transducer will be described in detail below.

Referring to FIGS. 2A–2D, sensor tip 14 is connected to a lower end portion 15 of an elastic sheath 16. The other end of sheath 16 partially extends into a portion of a neck extension 18. Sheath 16 is connected to neck extension 18 where sheath 16 intersects a lower surface 11 of neck extension 18. Sensor tip 14, sheath 16 and neck extension 18 are all immersed in fluid 6. Neck extension 18 extends through flange portion 4a and is connected to flange 8. Neck extension 18 is an inactive element that does not vibrate with sheath 16. Neck extension 18 serves to prevent stagnant flow regions from developing near the area of attachment of transducer 2 with pipe 4. Alternatively, the transducer may not have a neck extension attached to the flange. In such embodiments, the sheath is directly connected to the flange.

Transducer 2 includes a generally cylindrical support block 20 having four support struts 22, each cantileverly affixed with a ferrule 19 seated in a semicircular well 25 on an upper surface 21 of support block 20. The ferrules are secured in place with an annular ring 9. The ends 23 of support struts 22 distal from their respective ferrules are all secured to one end of a minor shaft 24 which is coaxially positioned and attached at its other end to an upper end of a hollow shaft 26. Hollow shaft 26 is disposed within, coaxially positioned with, spaced from, and extends through a hole 28 defined by flange 8, a hole 30 defined by neck extension 18 and sheath 16. A lower end of shaft 26 is connected to the lower end portion of sheath 16 to which sensor tip 14 is attached so that shaft 26 is essentially free floating within transducer 2 between the shaft's points of attachment with other parts of transducer 2. Minor shaft 24 extends through and is secured to a cross bar 34 by brazing. Attached to each end of cross bar 34 are a pair of disks 38 having a high magnetic permeability. Positioned over block 20 is a dust cover (not shown) to protect the interior components from debris. The dust cover is attached to block 20 and spaced from dome cover 13.

Support block 20 includes four magnetic coils 40a, 40b, 40c and 40d disposed within block 20, the pair of coils 40a and 40b being driver coils and the pair 40c and 40d being detector coils. Each magnetic coil is spaced from an adjacent disk 38 by a nominal gap of about 0.004 inch to about 0.012 inch.

Figure 3A:
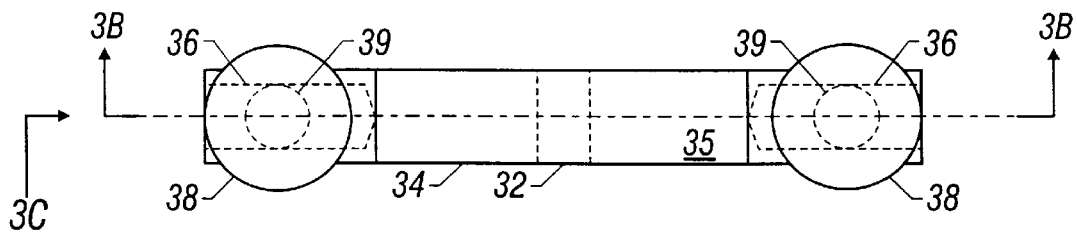
FIG. 3A is a side view of a cross bar used in the viscometer of FIG. 1.
Figure 3B:
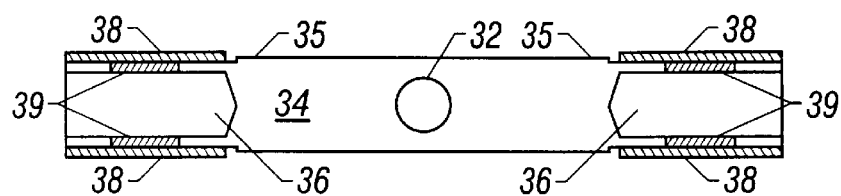
FIG. 3B is a top cross-sectional view of the cross bar taken along line 3B—3B.
Figure 3C:
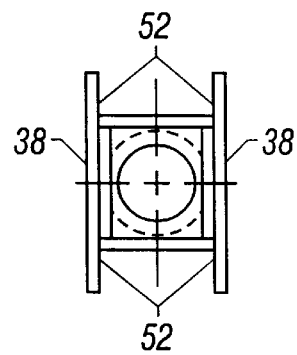
FIG. 3C is an end view of the cross bar taken along line 3C of FIG. 3A.

With further reference to FIGS. 3A–3C, cross bar 34 includes a hole 32 through which minor shaft 24 (FIG. 2B) is disposed, and two cylindrical hollow regions 36 for placement of balancing weights (not shown) within the hollow regions. Each disk 38 includes a seating tab 39 cooperatively positioned within a seating hole (not shown) defined on opposing sides 35 of cross bar 34. Each of the seating holes includes a chamber to aid in placement of the seating tabs.

Figure 4A:
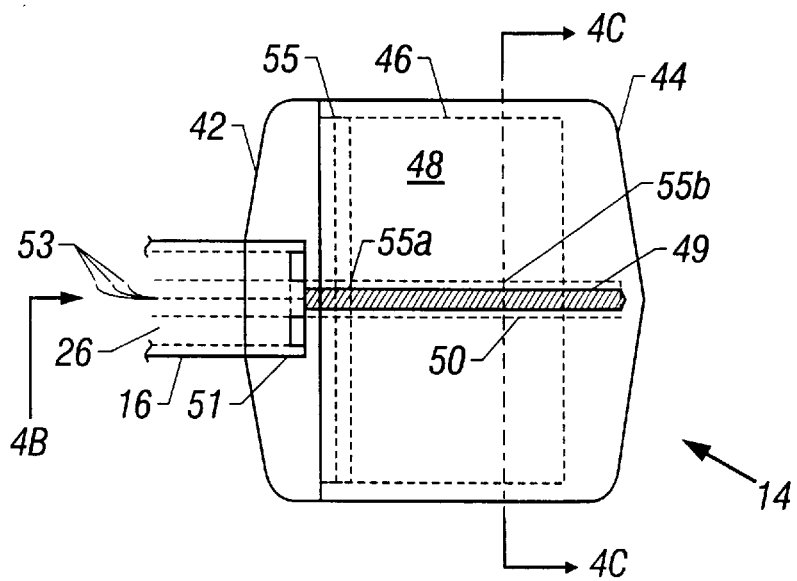
FIG. 4A is a side view of a sensor tip used in the viscometer of FIG. 1.
Figure 4B:
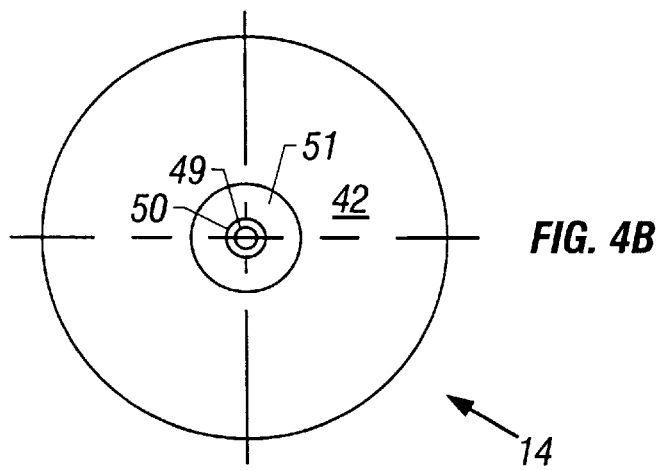
FIG. 4B is a top view of the sensor tip along line 4B of FIG. 4A.
Figure 4C:
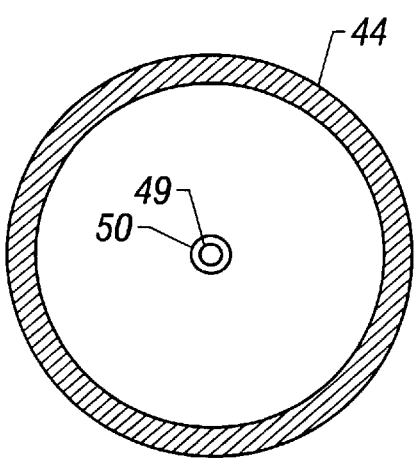
FIG. 4C is an end cross-sectional view of the sensor tip along line 4C—4C of FIG. 4A.

Referring now to FIGS. 4A–4C, sensor tip 14 includes a cap portion 42 in secured engagement (e.g. by press fitting and brazing) with a body portion 44. An inner surface 46 of sensor tip 14 defines a hollow region 48. Sensor tip 14 is sealed so that hollow region 48 is isolated from the fluid into which sensor tip 14 is immersed. A support tube 50 positioned coaxial with hollow shaft 26 extends from cap portion 42, is disposed within hollow region 48, and extends into a hole defined by body portion 44. Disposed within support tube 50 is a resistive thermal device (RTD) 49. RTD 49 includes a resistive platinum element encased in a ceramic jacket. The RTD is in contact with support tube 50 near the region in which support tube 50 extends into body portion 44 so that the RTD is thermally connected to body portion 44. RTD 49 includes three insulated leads 53 which are further covered with additional insulating material. The leads extend through hollow shaft 26 and are connected to controller 3.

Figure 5:
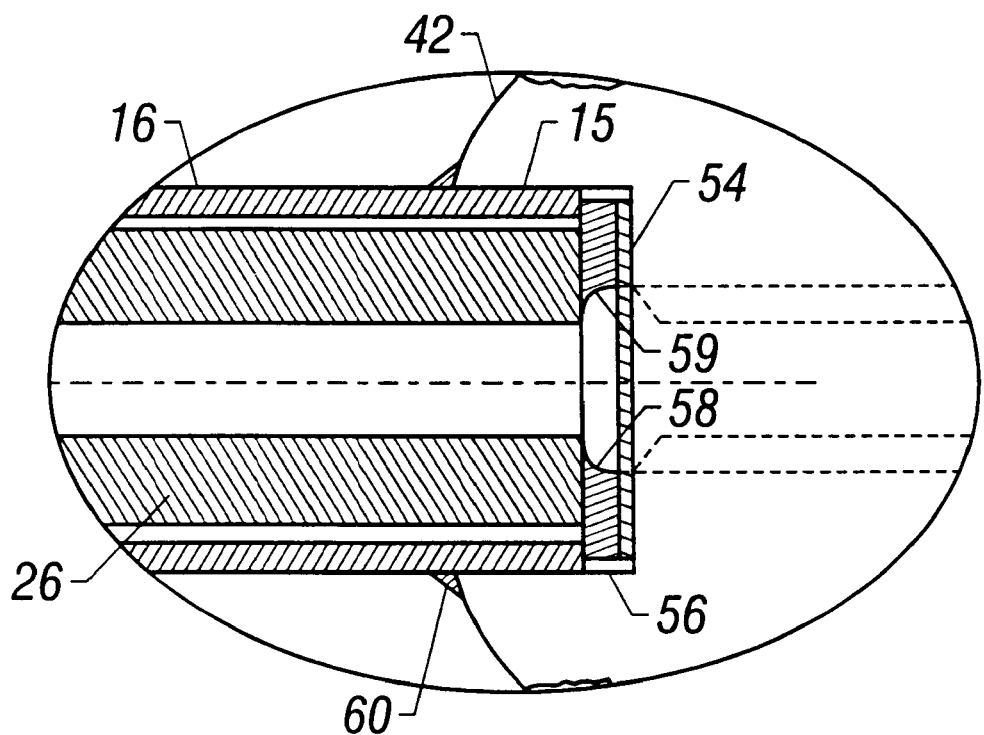
FIG. 5 is an enlarged side sectional view along the line 5—5 of FIG. 2B.

As shown in FIG. 5 and FIG. 4A, cap portion 42 has a bore 51 into which lower end portion 15 of sheath 16 is securely fitted and attached.

In the illustrated embodiment, flange 8, sensor tip 14, sheath 16 and neck extension 18 are made from 316 (or 316L) stainless steel. Support block 20, minor shaft 24, hollow shaft 26 and cross bar 34 are made from either 316 (or 316L) stainless steel or from 304 stainless steel. As such, sheath 16 is connected to neck extension 18 (or directly to flange 8 if there is no neck extension) by a braze and disks 38 are attached to cross bar 34 with brazes 52 shown in FIG. 3. Sensor tip 14, sheath 16 and neck extension 18 can also be made of a material having the composition (commonly referred to as HastelloyC): 54% Ni, 15.5% Cr, 15.5% Mo, 5.5% Fe, 2.5% Co, 7% other. The face of flange 8 facing the fluid may also be covered with a Hastelloy plate. The transducer components may also be made from other types of stainless steel.

Referring now to FIGS. 4A–4C, cap portion 42 is press fit into body portion 44 and secured with a braze 55, and support tube 50 is connected to cap portion 42 and body portion 44 with brazes 55a and 55b, respectively. With reference to FIG. 5, shaft 26 is connected to sheath 16 with an annular ring 54 which is attached to sheath 16 with a braze 56 disposed around the circumference of annular ring 54 and to shaft 26 with a braze 58 disposed around the inner surface 59 of ring 54. Cap portion 42 of sensor tip 14 is affixed to sheath 16 with a braze 60 disposed around the circumference of sheath 16. All the above described brazes are nickel based.

Support struts 22 are made from A2 tool steel, and disks 38 are made from a material having the composition 64% Fe, 36% Ni, commonly referred to as Invar. Each disk has a flat side (the sides opposite that of the seating tab) coated with boron nitride. Each magnetic coil, 40a to 40d, includes a stainless steel casing enclosing a permanent magnetic core made from, e.g., Alnico (55% Fe, 28% Ni, 12% Al, 5% Co) having insulated windings wound around the core. Suitable magnet coils are produced, for example, by Motion Sensors Inc., Elizabeth City, N.C. The casing includes a threaded portion in secured engagement with a threaded hole disposed on block 20. The casing is locked in place with a lock nut. The thread portion on the casing facilitates adjustment of the gap between each coil and adjacent disk 38.

The entire assembly, prior to placement of coils 40a to 40d, is annealed at a temperature of about 2000° C. to eliminate any residual stresses that may have been produced, for example, during the brazing or machining of the transducer's components.

In operation, sensor tip 14 of transducer 2 is immersed in a liquid shown in FIG. 1. Electrical power is supplied from drive circuit 105 of controller 3 to magnetic coils 40a and 40b to drive cross bar 34 back and forth across the gaps between the coils and adjacent disks 38. This causes minor shaft 24 and hollow shaft 26 to oscillate about their axes. This oscillation is transferred to sensor tip 14 causing sensor tip 14 to oscillate about its axis. The peak to peak oscillation amplitude is about 1 micron. Since sheath 16 is connected at one end to shaft 26 and at its other end to neck extension 18 (or flange 8 if neck extension 18 is not present), sheath 16 acts as a torsional return spring.

The viscous nature of the fluid dampens the oscillation of the sensor. Controller 3 of viscometer 1 compensates for changes in viscosity of the fluid flowing past the sensor tip by varying the power supplied to coils 40a and 40b to maintain the desired angular velocity of cross bar 34 and correspondingly the angular velocity of sensor tip 14. The angular velocity of the cross bar is detected by coils 40c and 40d and is electrically transmitted to detector circuit 107. The velocity signals are transmitted to feedback circuit 109 and compared with a reference signal. The drive current is then adjusted accordingly to maintain the desired velocity. Process temperatures and variations in temperature are detected with the RTD disposed within sensor tip 14, the signal from the RTD being fed back into controller 3. Accurate temperature readings are essential since fluid viscosities are often extremely sensitive to temperature. Also, the thermal mass of the hollow sensor tip is much less than that of a solid tip having the same size. This feature reduces the response time associated with accurately measuring the fluid temperature.

In the illustrated embodiment, the viscosity-density product of the fluid is measured directly with the viscometer. Sensor tip 14 is about 1 inch long and about 1.5 inches in diameter. With a sensor tip of this size and with a known or measurable fluid density, the viscometer can measure fluid viscosities in the range from about 1 cP to about 10,000 cP.

The sensor tip can have different sizes and shapes. For example, the sensor tip can be about 2 inches long and about 1.5 inches in diameter. In use, such a sensor tip enables the viscometer to measure fluid viscosities in the range from about 0.1 cP to about 1,000 cP.

Figure 6A:
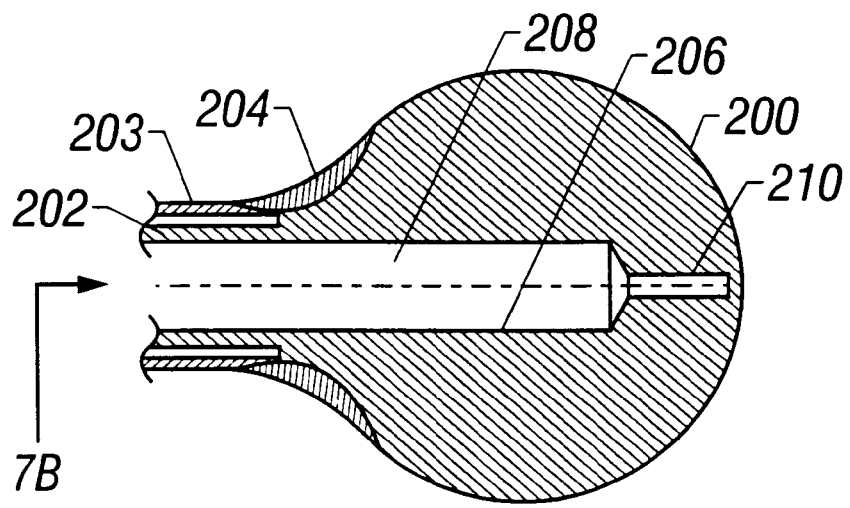
FIG. 6A is a side view of an alternate embodiment of a sensor tip that can be used in the viscometer of FIG. 1.
Figure 6B:
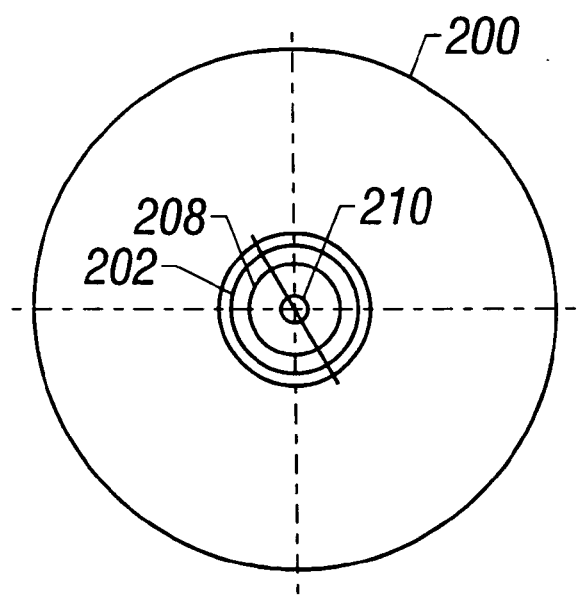
FIG. 6B is a top view of the hollow spherical sensor tip taken along line 6B.

Referring now to FIGS. 6A and 6B, a spherical sensor tip 200 is integral to a shaft 202. Similar to that described above, sensor tip 200 is connected to a sheath 203 by brazes 204. An inner surface 206 of sensor tip 200 defines a hollow region 208. Sensor tip 200 also defines a hollow bore 210 into which a support tube (not shown) for an RTD is positioned. The RTD is positioned inside the support tube. Alternatively, the RTD can be positioned directly inside hollow bore 210. A viscometer having sensor tip 200 is capable of measuring fluid viscosities in the range from about 1 cP to about 100,000 cP.

Many additional embodiments are possible. The is transducer can be used to measure the viscosity of fluids in reactor tanks. The transducer may be positioned in such a way that the sensor tip extends perpendicularly to the general direction of the flow path of the fluid. The RTD may be disposed within a sensor tip that does not have a hollow support tube. Support block 20 may include a RTD mounted to the interior of block 20 so that the temperature of the region near the coils can be monitored. Instead of brazing the transducer parts together as described above, certain parts may be welded together, in particular the parts exposed to the fluid such as the sensor tip, sheath, neck extension and flange surface facing the fluid. Alternatively, these parts can be dress welded together by first brazing and applying a weld on top of the brazed areas.

Other embodiments are within the following claims.

What is claimed is:

1. A sensor tip for a viscometer comprising:
 a cylindrical member having an inner surface defining a hollow region and an opening to said hollow region, the member being configured for oscillation for viscosity measurement; and
 a sensor disposed within the sensor tip;
 the sensor tip being rigidly attached to a hollow cylindrical sheath having a shaft disposed therein, the shaft having a distal end Portion connected to a distal end portion of the sheath.

2. The sensor tip of claim 1 wherein said cylindrical member is a composite member having a body portion providing said inner surface defining said hollow region and a cap portion, said cap portion having a bore defining said opening, said sensor tip further comprising:
 a hollow shaft; and
 a hollow sheath disposed around said hollow shaft, said hollow sheath having an end portion connected to the end portion of said shaft and connected to the cylindrical member at the bore.

3. The sensor tip of claim 2 wherein said shaft and said sheath are disposed through said opening to said hollow region in the tip.

4. The sensor tip of claim 1 further comprising a support tube disposed within the sensor tip, the sensor being disposed within said support tube.

5. The sensor tip of claim 4 wherein said sensor is a temperature sensor.

6. The sensor tip of claim 1 wherein said member is sealed so that said hollow region is isolated from a fluid into which said member is immersed.

7. The sensor tip of claim 5 wherein the temperature sensor is a resistive thermal device.

8. The sensor tip of claim 7 wherein the member having an inner surface defining a hollow region and a hollow bore is a spherical member.

9. The sensor tip of claim 7 wherein the sensor is a temperature sensor.

10. A sensor tip for a viscometer comprising:
 a member having an inner surface defining a hollow region and a hollow bore, said hollow bore configured to hold a sensor, said member being sealed so that said hollow region and said hollow bore are isolated from a fluid into which said member is immersed, the member being configured for oscillation for viscosity measurement.

11. The sensor tip of claim 10 further comprising a support tube disposed within said hollow bore, said sensor being positioned within said support tube.

12. The sensor tip of claim 10 further comprising a sensor disposed within said hollow bore.

13. A transducer for a vibratory viscometer, comprising:
 a hollow cylindrical sheath;
 a hollow cylindrical shaft disposed within said cylindrical sheath, said shaft having a first end portion and a second end portion connected to a distal end portion of said sheath;
 a sensor tip rigidly attached to said distal end portion of said sheath, said sensor tip having an inner surface defining a hollow region, the sensor tip being configured for oscillation for viscosity measurement;
 a support tube disposed within said hollow region, said support tube configured to hold a sensor; and
 a crossbar coupled to said first end portion of said shaft.

14. The transducer of claim 13 wherein said sensor tip is cylindrical.

15. The transducer of claim 14 wherein said sensor tip includes a cap portion and a body portion, said body portion providing said inner surface defining said hollow region.

16. The transducer of claim 15 wherein said support tube extends from said cap portion through said hollow region and into a portion of said body portion.

17. The transducer of claim 16 wherein said shaft is hollow and said sensor has leads extending through the hollow shaft.

18. The transducer of claim 17 wherein said sensor is a temperature sensor.

19. The transducer of claim 13 wherein said sensor tip is spherical.

20. The sensor tip of claim 18 wherein the temperature sensor is a resistive thermal device.

21. A transducer for a vibratory viscometer, comprising:

a hollow cylindrical sheath;

a hollow cylindrical shaft disposed within said cylindrical sheath, said shaft having a first end portion and a second end portion connected to a distal end portion of said sheath;

a sensor tip connected to said distal end portion of said sheath, said sensor tip having an inner surface defining a hollow region;

a support tube disposed within said hollow region, said support tube configured to hold a sensor;

a crossbar coupled to said first end portion of said shaft; and a neck extension having a lower end connected to said sheath, said neck extension defining a hole between an upper end of said neck extension and said lower end, said extension being positioned so that said hole is substantially coaxially aligned with said sheath and said shaft.

22. Transducer for a vibratory viscometer, comprising:

a hollow cylindrical sheath;

a hollow cylindrical shaft disposed within said cylindrical sheath, said shaft having a first end portion and a second end portion connected to a distal end portion of said sheath;

a sensor tip connected to said distal end portion of said sheath, said sensor tip having an inner surface defining a hollow region;

a support tube disposed within said hollow region, said support tube configured to hold a sensor;

a crossbar coupled to said first end portion of said shaft; and a high magnetically permeable member disposed on said cross bar.

23. The transducer of claim 22 wherein said transducer further comprises:

a pair of spaced apart magnetic driver coils near a first end of said cross bar, each of said driver coils spaced from an adjacent high magnetically permeable member on said cross bar; and a pair of spaced apart magnetic detector coils near a second end of said cross bar, each of said detector coils spaced from an adjacent high magnetically permeable member on said cross bar, said driver coils are connected to a drive circuit, said driver circuit supplying electrical power to said driver coils, thereby creating a magnetic force to cause the rotational oscillation of said sensor tip, said detector coils connected to a detector circuit configured to detect an electrical signal related to the motion of sensor tip, said driver circuit and said detector circuit configured to supply signals to a feedback circuit, said feedback circuit configured to supply a correction signal to said driver circuit so that said oscillation remains substantially at a desired angular velocity.

24. The transducer of claim 13 wherein said sheath and said sensor tip are made of 316 stainless steel.

25. A transducer for a vibratory viscometer, comprising:

a hollow cylindrical sheath;

a hollow cylindrical shaft disposed within said cylindrical sheath, said shaft having a first end portion and a second end portion connected to a distal end portion of said sheath;

a sensor tip connected to said distal end portion of said sheath, said sensor tip having an inner surface defining a hollow region;

a support tube disposed within said hollow region, said support tube configured to hold a sensor;

a crossbar coupled to said first end portion of said shaft; and wherein said sheath and said sensor tip are made of HastelloyC.

26. A transducer for a vibratory viscometer, comprising:

a hollow cylindrical sheath;

a hollow cylindrical shaft disposed within said cylindrical sheath, said shaft having a first end portion and a second end portion connected to a distal end portion of said sheath;

a sensor tip connected to said distal end portion of said sheath, said sensor tip having an inner surface defining a hollow region, the sensor tip being configured for oscillation for viscosity measurement;

a support tube disposed within said hollow region, said support tube configured to hold a sensor; and a crossbar coupled to said first end portion of said shaft;

wherein a connection between said sheath and said sensor tip is welded.

27. The transducer of claim 22 wherein said magnetically permeable member is comprised of Invar.

28. A method of measuring viscosity of a fluid comprising the steps of:

providing a transducer with a hollow sensor tip having a support tube and a sensor disposed within the support tube, and with said support tube disposed within said sensor tip, the sensor tip being rigidly attached to a hollow cylindrical sheath and being configured for oscillation for viscosity measurement;

immersing said sensor tip into said fluid;

driving said transducer with electrical power causing said sensor tip to oscillate about an axis of said sensor tip, by driving a shaft disposed within the sheath and having a distal end portion connected to a distal end portion of the sheath;

maintaining the oscillation of said sensor tip at a predetermined angular velocity by varying said electrical power; and correlating said electrical power with said viscosity.

* * * * *